US00PP23964P2

(12) United States Plant Patent
Pieters

(10) Patent No.: US PP23,964 P2
(45) Date of Patent: Oct. 8, 2013

(54) ***CHRYSANTHEMUM* PLANT NAMED 'MAGNUS VIOLET'**

(50) Latin Name: *Chrysanthemem×morifolium*
Varietal Denomination: Magnus Violet

(75) Inventor: Dirk Pieters, Oostnieuwkerke (BE)

(73) Assignee: Paraty B.V.B.A., Oostnieuwkerke (BE)

( * ) Notice: Subject to any disclaimer, the term of this patent is extended or adjusted under 35 U.S.C. 154(b) by 4 days.

(21) Appl. No.: 13/385,748

(22) Filed: Mar. 5, 2012

(51) Int. Cl.
*A01H 5/00* (2006.01)

(52) U.S. Cl.
USPC ..... Plt./287

(58) Field of Classification Search
USPC ..... Plt./287, 292
See application file for complete search history.

*Primary Examiner* — Kent L Bell
(74) *Attorney, Agent, or Firm* — C. A. Whealy

(57) ABSTRACT

A new and distinct cultivar of *Chrysanthemum* plant named 'Magnus Violet', characterized by its upright, outwardly spreading and rounded plant habit; moderately vigorous growth habit; freely branching habit; dense and full plant habit; large dark green-colored leaves; uniform, early and freely flowering habit; large decorative-type inflorescences with purple-colored ray florets; and excellent garden performance.

1 Drawing Sheet

Botanical designation: *Chrysanthemum×morifolium*.
Cultivar denomination: 'MAGNUS VIOLET'.

BACKGROUND OF THE INVENTION

The present invention relates to a new and distinct cultivar of *Chrysanthemum* plant, botanically known as *Chrysanthemum×morifolium*, and hereinafter referred to by the name 'Magnus Violet'.

The new *Chrysanthemum* plant is a product of a planned breeding program conducted by the Inventor in Oostnieuwkerke, Belgium. The objective of the breeding program is to create new freely flowering *Chrysanthemum* plants with unique and attractive ray floret coloration.

The new *Chrysanthemum* plant originated from a cross-pollination made by the Inventor in Oostnieuwkerke, Belgium in September, 2005 of *Chrysanthemum×morifolium* 'Perano', not patented, as the female, or seed, parent with *Chrysanthemum×morifolium* 'Cassano', not patented, as the male, or pollen, parent. The new *Chrysanthemum* plant was discovered and selected by the Inventor as a flowering plant from within the progeny of the stated cross-pollination in a controlled greenhouse environment in Oostnieuwkerke, Belgium in September, 2006.

Asexual reproduction of the new *Chrysanthemum* plant by vegetative cuttings was first conducted in a controlled greenhouse environment in Oostnieuwkerke, Belgium in January, 2007. Asexual reproduction by cuttings has shown that the unique features of this new *Chrysanthemum* plant are stable and reproduced true to type in successive generations.

SUMMARY OF THE INVENTION

Plants of the new *Chrysanthemum* have not been observed under all possible environmental conditions and cultural conditions. The phenotype may vary somewhat with variations in environmental conditions such as temperature, daylength and light intensity, without, however, any variance in genotype.

The following traits have been repeatedly observed and are determined to be the unique characteristics of 'Magnus Violet'. These characteristics in combination distinguish 'Magnus Violet' as a new and distinct *Chrysanthemum* plant:

1. Upright, outwardly spreading and rounded plant habit; moderately vigorous growth habit.
2. Freely branching habit; dense and full plant habit.
3. Large dark green-colored leaves.
4. Uniform, early and freely flowering habit.
5. Large decorative-type inflorescences with purple-colored ray florets.
6. Excellent garden performance.

Plants of the new *Chrysanthemum* differ primarily from the female parent, 'Perano', in the following characteristics:

1. Plants of the new *Chrysanthemum* are not as vigorous as plants of 'Perano'.
2. Plants of the new *Chrysanthemum* have larger leaves than plants of 'Perano'.
3. Plants of the new *Chrysanthemum* have larger inflorescences than plants of 'Perano'.
4. Plants of the new *Chrysanthemum* flower slightly later than plants of 'Perano'.

Plants of the new *Chrysanthemum* differ primarily from the male parent, 'Cassano', in the following characteristics:

1. Plants of the new *Chrysanthemum* are not as vigorous as plants of 'Cassano'.
2. Plants of the new *Chrysanthemum* have larger inflorescences than plants of 'Cassano'.
3. Plants of the new *Chrysanthemum* flower earlier than plants of 'Cassano'.
4. Ray florets of plants of the new *Chrysanthemum* are darker in color than plants of 'Cassano'.

Plants of the new *Chrysanthemum* can also be compared to plants of *Chrysanthemum×morifolium* 'Yobeth', disclosed in U.S. Plant Pat. No. 11,818. In side-by-side comparisons conducted in Oostnieuwkerke, Belgium, plants of the new *Chrysanthemum* differed from plants of 'Yobeth' in the following characteristics:

1. Plants of the new *Chrysanthemum* were more rounded in shape than plants of 'Yobeth'.
2. Plants of the new *Chrysanthemum* were more flexible than and not as brittle as plants of 'Yobeth'.
3. Inflorescences of plants of the new *Chrysanthemum* were more double than inflorescences of plants of 'Yobeth'.

BRIEF DESCRIPTION OF THE PHOTOGRAPH

The accompanying photograph illustrates the overall appearance of the new *Chrysanthemum* plant showing the colors as true as it is reasonably possible to obtain in colored reproductions of this type. Colors in the photograph may differ slightly from the color values cited in the detailed botanical description which accurately describe the colors of the new *Chrysanthemum* plant.

The photograph comprises a side perspective view of a typical flowering plant of 'Magnus Violet' grown in a container.

DETAILED BOTANICAL DESCRIPTION

The aforementioned photograph and following observations and measurements describe plants grown in 19-cm containers during the late summer and early autumn in an outdoor nursery in Oostnieuwkerke, Belgium and under cultural practices which approximate those generally used in commercial *Chrysanthemum* production. During the production of the plants, day temperatures ranged from 25° C. to 30° C. and night temperatures ranged from 15° C. to 20° C. Plants were 20 weeks old when the photograph and detailed description were taken. In the following description, color references are made to The Royal Horticultural Society Colour Chart, 2005 Edition, except where general terms of ordinary dictionary significance are used.

Botanical classification: *Chrysanthemum×morifolium* 'Magnus Violet'.

Parentage:

*Female, or seed, parent.*—*Chrysanthemum×morifolium* 'Perano', not patented.

*Male, or pollen, parent.*—*Chrysanthemum×morifolium* 'Cassano', not patented.

Propagation:

*Type.*—Terminal vegetative cuttings.

*Time to initiate roots, summer.*—About 14 days at temperatures of about 20° C.

*Time to initiate roots, winter.*—About 20 days at temperatures of about 20° C.

*Time to produce a rooted young plant, summer.*—About 30 days at temperatures of about 20° C.

*Time to produce a rooted young plant, winter.*—About 40 days at temperatures of about 20° C.

*Root description.*—Fine, fibrous; light brown in color.

*Rooting habit.*—Freely branching; medium density.

Plant description:

*Appearance.*—Perennial decorative-type *Chrysanthemum*; stems upright and outwardly spreading giving a uniformly rounded appearance to the plant; plants roughly spherical; very freely branching habit, about 25 to 30 primary lateral branches develop, each primary lateral branch with multiple secondary branches; pinching enhances lateral branch development; dense and full plant habit; moderately vigorous growth habit; plants flexible, not brittle.

*Plant height.*—About 45 cm.

*Plant width.*—About 50 cm.

*Lateral branches.*—Length: About 20 cm to 25 cm. Diameter: About 2 mm to 3 mm. Internode length: About 2.5 cm. Strength: Strong, flexible. Texture: Pubescent; longitudinally ridged. Color: Close to 137A.

*Leaves.*—Arrangement: Alternate, simple. Length: About 4.5 cm to 7 cm. Width: About 3.5 cm to 4 cm. Apex: Rounded to cuspidate. Base: Attenuate. Margin: Palmately lobed and serrate, sinuses between lateral lobes divergent to parallel. Texture, upper and lower surfaces: Slightly pubescent. Color: Developing leaves, upper surface: Close to 137C. Developing leaves, lower surface: Close to 139C. Fully expanded leaves, upper surface: Close to 137A; venation, close to 148C. Fully expanded leaves, lower surface: Close to 137C; venation, close to 147B to 147C. Petiole: Length: About 1 cm. Diameter: About 2 mm. Texture, upper and lower surfaces: Slightly pubescent and rough. Color, upper surface: Close to 137C. Color, lower surface: Close to 137D.

Inflorescence description:

*Appearance.*—Decorative inflorescence form; inflorescences borne on terminals above foliar plane; disc and ray florets arranged acropetally on a capitulum.

*Fragrance.*—Slightly fragrant, pungent.

*Flowering response.*—Under natural season conditions, plants flower in mid-September in Belgium; flowering response time, about five weeks.

*Postproduction longevity.*—Inflorescences maintain good color and substance for about six weeks in an outdoor nursery; inflorescences persistent.

*Quantity of inflorescences.*—About 30 inflorescences develop per lateral branch.

*Inflorescence bud.*—Height: About 5 mm to 7 mm. Diameter: About 8 mm to 10 mm. Shape: Globular. Color: Close to 137C.

*Inflorescence size.*—Diameter: About 4 cm. Depth (height): About 6 cm. Disc diameter: About 3 mm. Receptacle diameter: About 3 mm. Receptacle height: About 2.5 mm to 3 mm. Receptacle color: Close to 144B.

*Ray florets.*—Length: About 4.5 cm to 5.5 cm. Width: About 5 mm to 7 mm. Shape: Oval. Apex: Rounded. Base: Attenuate. Margin: Entire. Aspect: Mostly flat. Texture, upper and lower surfaces: Smooth, glabrous. Number of ray florets per inflorescence: About 150 to 200 arranged in about ten whorls. Color: When opening, upper surface: Close to 72B. When opening, lower surface: Close to 70B. Fully opened, upper surface: Close to 77B; color becoming closer to 76B with development. Fully opened, lower surface: Close to N82C; color becoming closer to 76B with development.

*Disc florets.*—Length: About 3 mm. Diameter: About 0.5 mm to 1 mm. Shape: Tubular, elongated; apices acute. Number of disc florets per inflorescence: About 20 massed at the center of the inflorescence. Color, immature: Close to 145A. Color, mature: Close to 12A.

*Phyllaries.*—Number of phyllaries per inflorescence: About 25 arranged in two or three whorls. Length: About 4 mm to 6 mm. Width: About 2 mm to 3 mm. Shape: Ovate. Apex: Rounded. Base: Rounded to truncate. Margin: Entire. Texture, upper and lower surfaces: Smooth, glabrous. Color, upper surface: Close to 137A. Color, lower surface: Close to N137B.

*Peduncles*.—Length, terminal peduncle: About 5 cm. Length, fourth peduncle: About 5 cm. Length, seventh peduncle: About 5 cm. Diameter: About 3 mm. Angle: About 30° from vertical. Strength: Moderately strong. Texture: Slightly pubescent. Color: Close to 137C.

*Reproductive organs*.—Androecium: Not observed. Gynoecium: Not observed.

*Seeds and fruits*.—Seed and fruit production have not been observed on plants of the new *Chrysanthemum*.

Disease & pest resistance: Resistance to pathogens and pests common to *Chrysanthemums* has not been observed on plants grown under commercial conditions.

Garden performance: Plants of the new *Chrysanthemum* have demonstrated excellent garden performance and will tolerate temperatures ranging from about 0° C. to about 45° C.

It is claimed:

1. A new and distinct *Chrysanthemum* plant named 'Magnus Violet' as illustrated and described.

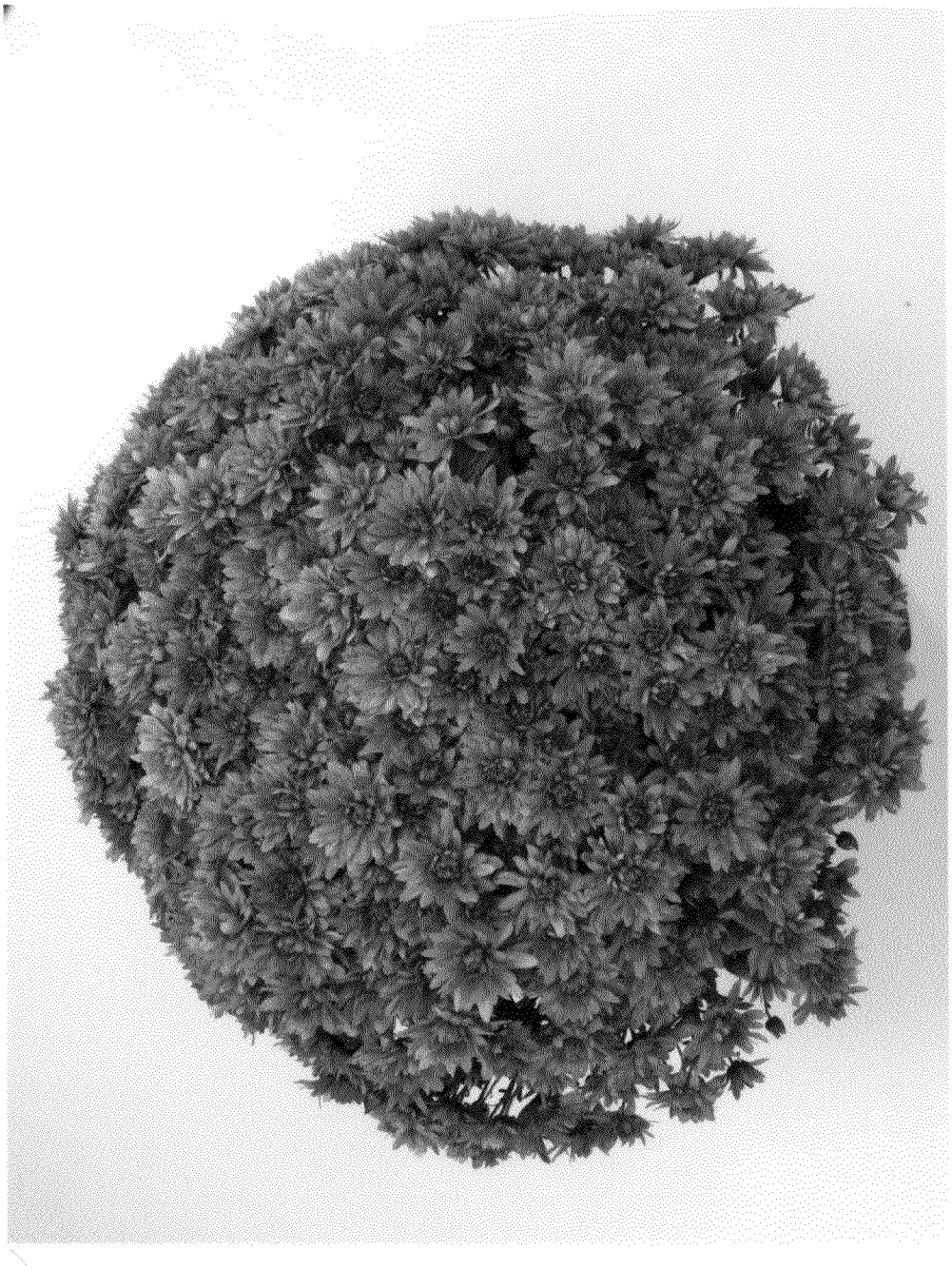

* * * * *